United States Patent [19]
Ladisch et al.

[11] Patent Number: 5,808,010
[45] Date of Patent: Sep. 15, 1998

[54] METHOD FOR DERIVATIZATION OF CELLULOSIC STATIONARY PHASE

[75] Inventors: Michael Ladisch; Christine Ladisch, both of West Lafayette; Karen Kohlmann, Carmel; Ajoy Velayudhan; Richard Hendrickson, both of West Lafayette, all of Ind.; Paul Westgate, Columbia, Md.; Jiyin Liu, West Lafayette, Ind.

[73] Assignee: Purdue Research Foundation, West Lafayette, Ind.

[21] Appl. No.: 485,839

[22] Filed: Jun. 7, 1995

Related U.S. Application Data

[62] Division of Ser. No. 260,022, Jun. 15, 1994, abandoned.

[51] Int. Cl.$^6$ .............................. C07K 1/16; C07K 1/18; C08J 7/12; C12S 11/00
[52] U.S. Cl. ................................. 530/415; 8/181; 8/188; 8/401; 521/29; 521/30; 527/312; 530/413; 530/416; 530/417
[58] Field of Search ..................... 530/415, 412, 530/417, 363, 413, 416; 8/116.1, 181, 188, 401; 435/803, 96; 422/212, 222; 521/27, 29, 30; 527/103, 312

[56] References Cited

U.S. PATENT DOCUMENTS

| | | | |
|---|---|---|---|
| 1,777,970 | 10/1930 | Hartmann | 536/43 |
| 4,818,598 | 4/1989 | Wong | 428/326 |
| 4,912,056 | 3/1990 | Olson | 435/263 |
| 5,001,063 | 3/1991 | Antrim et al. | 435/179 |
| 5,232,851 | 8/1993 | Cox et al. | 435/263 |

OTHER PUBLICATIONS

Biotechnology and Bioengineering, vol. 25, issued 1983, Boyer et al., "Effect of Chemical Modification of Cellulose on the Activity of a Cellulose from *Aspergillus niger*", pp. 1311–1319, see especially pp. 1312 and 1313.

"Biochemicals, Organic Compounds for Research and Diagnostic Reagents", published 1990 by Sigma Chemical Company, see p. 1568.

Advances in Biochemical Engineering, Biotechnology, vol. 49, issued 1993, Yang et al "Liquid Chromatography Using Cellulosic Continuous Stationary Phases", pp. 147–160, see especially pp. 154–156.

Schubert, W.M. and Zahler, R.E., "Aromatic Electrophilic Substitution by Hydrogen. III. The Mechanism of the Acid–Catalyzed Decarboxylation of Aromatic Aldehydes$^2$", J. of the Amer. Chem. Soc., vol. 76, pp. 1711–1712 (1954).

Tsuei, A.C.R. and Yang, V.C., "Ion–Exchange Hollow Fibers", Amer. Chem. Soc., vol. 31, No. 1, pp. 238–239 (1990).

Kumar, A., "Enzymatic Finishing of Lyocell Fabrics", Book of Papers; 1994 International Conference & Exhibition, Amer. Assoc. of Textile Chemists and Colorists (Abstract), Genencor International Inc., South San Francisco, California, p. 488 (1994).

Hoffpauir, C.L. and Guthrie, J.D., "Ion–Exchange Characteristics of Chemically Modified Cotton Fabrics", Textile Res. J., vol. 20, pp. 617–620 (1950).

James, K. and Stanworth, D.R., "Studies on the Chromatography of Human Serum Protein on Deithylamino–Ethyl (DEAE)—Cellulose I. The Effect of the Chemical and Physical Nature of the Exchanger", J. Chromatogr., vol. 15, pp. 324–335 (1964).

(List continued on next page.)

*Primary Examiner*—Jeffrey E. Russel
*Attorney, Agent, or Firm*—Woodard, Emhardt, Naughton, Moriarty & McNett

[57] ABSTRACT

A solid sorbent material comprising cellulose which has been modified by hydrolysis with a cellulase enzyme for a duration sufficient to increase the protein adsorption capacity of the solid sorbent material and methods for preparing the sorbent material. Methods for purifying a protein include passing a liquid medium containing the protein over the solid sorbent material are also included.

19 Claims, 4 Drawing Sheets

Effect of Enzyme Treatment on Loading
BSA-6003 on DE 3764

OTHER PUBLICATIONS

Knight, C.S., "Some Fundamentals of Ion–Exchange–Cellulose Design and Usage in Biochemistry", Advances in Chromatography, vol. 4, Giddings, J.C. and Keller, R.A. (eds.), Marcel Dekker, Inc., New York, NY, pp. 61–110 (1967).

Peterson, E.Q. and Sober, H.A., "Chromatography of Proteins I. Cellulose Ion–Exchange Adsorbents", J. Am. Chem. Soc., vol. 78, pp. 751–755 (1956).

Roberts, E.J., Bose, J.L. and Rowland, S.P., "Evidence for Two Types of Accessible Surfaces in Fibrous Cotton", Textile Res. J., vol. 42, pp. 217–221 (1972).

Yang, Y., Velayudhan, A., Ladisch, C.M. and Ladisch, M.R., "Protein Chromatography Using a Continuous Stationary Phase", J. Chromatogr., vol. 598, pp. 169–180 (1992).

Guthrie, J.D., and Bullock, A.L., "Ion Exchange Celluloses for Chromatographic Separation", Ind. Eng. Chem., vol. 52, pp. 935–937 (1960).

Rowland, S.P., Roberts, E.J., and Wade, C.P., "Selective Accessibilities of Hydroxyl Groups in the Microstructure of Cotton Cellulose", Textile Research J., vol. 39, pp. 530–542 (1969).

Soignet, D.M., Berni, R.J., and Benerito, R.R., "Comparison of Properties of Anion–Exchange Cottons in Fabric Form", Textile Research J., vol. 36, pp. 978–989 (1966).

Roy, D. and Knoigsbert, W., "Chromatography of Proteins and Peptides on Diethylaminoethyl Cellulose", Methods in Enzymology, vol. XXV, Enzyme Structure, Part B., Hirs, C.H.W. and Timasheff, S.N. Editors, Chapter 17, pp. 221–231 (1972).

Sober, H.A., Gutter, F.J., Wyckoff, M.M., and Peterson, E.A., "Chromatography of Proteins II. Fractionation of Serum Protein on Anion–Exchange Cellulose", J. of the Amer. Chem. Soc., vol. 78, pp. 756–763 (1955).

METHOD FOR DERIVATIZATION OF CELLULOSIC STATIONARY PHASE

This application is a division of application Ser. No. 08/260,022, filed Jun. 15, 1994, now abandoned.

This invention was made with Government support under Grant No. NAGW-2329, awarded by the National Aeronautics and Space Administration. The Government has certain rights in the invention.

FIELD OF THE INVENTION

The present invention resides generally in the field of chromatography. The invention more specifically relates to stationary phases for use in chromatographic separations.

BACKGROUND OF THE INVENTION

Chromatography is a widely used method for separating, detecting and analysing mixtures of chemical compounds. The compound to be analysed is contained in a mobile phase which is passed through a column containing a solid, stationary phase. Traditionally such stationary phases have comprised a particulate material. The chemical or biochemical compounds injected in the mobile phase exhibit different retention times in the chromatographic column due to differences in affinity for the stationary phase. In this manner, various materials in the mobile phase are separated.

Separation costs in the manufacture of proteins and other biotechnology products are estimated to be well over 40% of the total production cost. The high cost of downstream processing may contribute to the high prices of selected therapeutic proteins (Knight, 1989). Key objectives towards improving the cost-effectiveness of chromatographic processes include reduction of the number and/or complexity of production steps and automation to reduce labor costs. Major improvements are required in separations technology, particularly in reducing residence time.

Derivatized cellulose particles are widely used in industry for ion exchange chromatography, protein purification, and enzyme immobilization. For protein purification, diethylaminoethyl (DEAE) cellulose materials or anion dextran gels are particularly desiriable due to their compatibility with proteins. However, packed columns of these soft particles cannot withstand a high pressure drop and, therefore, must be run at low flow rates. These flow rates are generally equivalent to interstitial velocities of less than 10 cm/min. Separations at these flow rates require hours, or longer, to complete, leading to undesirably long residence times.

Fibers and yarns can also be packed into chromatography columns such as liquid chromatography (LC) columns. The advantages of using fibrous beds are that the polymers which form fibers are chemically stable. Thus, changes in eluent composition will not easily damage the stationary phase. In addition, the pressure drop can be lower than for beds packed with ordinary particles, so that higher eluent flow rates can be used, if needed, while keeping pressure drop at a reasonable level. The fibrous form has a lower capacity and takes longer to reach equilibrium, but permits a faster flow rate and is more physically stable than the microgranular form (Roy and Konigsberg, 1972).

The use of fabrics for stationary phases has great potential. The term "fabric" in this context means a textile structure composed of mechanically interlocked fibers or filaments. Fabrics are either randomly integrated (nonwoven) or closely oriented by warp and filler strands at right angles to each other (woven). Since this type of stationary phase is a continuous matrix, it is referred to as a continuous stationary phase.

The fabric, if packed in a "tight" manner, retains the advantage of lower pressure drop of a fiber based stationary phase, and in addition gives the sorbent a diameter characteristic which is analogous to a monodisperse particulate stationary phase, but at a fraction of the cost of existing stationary phases. Since the diameter of the yarn and the density of the fabric are almost, the same in any place of the fabric, the geometry of the stationary phase is also similar in any place of the column, i.e., uniform packing is assured. The fibers in the yarns are closely related with each other in both warp and filling directions, and give mechanical support of the fabric when packed into the column. A fabric stationary phase is therefore resistant to compaction at high pressure and flow rate. Derivitization of the fabric is readily carried out, and can be easily done on a large scale using existing, and cost effective manufacturing techniques associated with dyeing, crosslinking, or finishing of textile yarns and fabrics.

Attractive features of a DEAE cellulosic fabric stationary phase include: inexpensive starting materials, convenient packaging of the resulting stationary phase, chemical and mechanical stability, and capability to achieve high flow rates. This new type of stationary phase has the potential to retain all the advantages of chromatography based on cellulosic ion exchangers, while avoiding the disadvantage of restricted flow rates and lack of mechanical stability associated with packed beds of cellulose particles. However, low protein binding capacity is a major limitation.

Both batch and continuous methods have been used for the preparation of DEAE-cellulose fabric stationary phase. In each process, differences may exist in the sources of cellulose such as wood and cotton and product forms such as fibrous and granular.

The earliest batch method developed by Hartman (1930) was carried out by wetting cotton fabric with 10% 2-(diethylamino)ethyl chloride, drying, and then mercerizing with 25% NaOH at room temperature overnight to obtain a cellulose with an exchange capacity of 0.25 meq/dry gram (Soignet et al., 1966).

Rowland et al., (1969), modified Hartman's method by treating it continuously in a padder through 2 dips and 2 nips with 1M solution of 2-(diethylamino)ethyl chloride, and then immersing the impregnated fabric into 1N NaOH for 45 minutes at room temperature. The product had a degree of substitution (DS) of 0.034 which corresponds to 0.29% nitrogen content (Roberts et al., 1972). Although the maximum capacity is considerably below that of granular ion exchangers, the chemical and physical stability of the DEAE-cellulose form of the fabric was maintained. The advantage offered by the enhanced physical stability of a fabric form of ion-exchanger was viewed to compensate for the much lower capacity of this type of material (Hoffpauir and Guthrie, 1950).

Mercerizing the cotton fabric prior to the DEAE treatment was found to improve the degree of substitution, and therefore, the ion exchange capacity. However, Rowland et al., (1969), reported that the total degree of substitution on the D-glucopyranosyl unit decreased as the concentration of sodium hydroxide increased from 2 to 6.1N. Hence, perceived benefits of mercerization were restricted to a relatively narrow NaOH concentration range. Mercerization of a fabric may take place either in hot or in ambient temperature NaOH solutions (Tsuei and Yang, 1990). In a recent study by Yang et al. (1993), DEAE-cellulose made from cotton fabric by a variation of the Rowland method (1969) separated BSA, IgG, insulin, and β-galactosidase in 9 minutes. A batch method for derivatizing wood cellulose (Polycel and Solka-Floc) was developed by Peterson and Sober (1956). First, the wood cellulose was stirred into a 20% NaOH solution and the mixture immersed in an ice bath for 30 minutes. Then 43.7% 2-(diethylamino)ethyl chloride was added in several portions. The mixture was immersed in an 80°–85° C. oil bath for 35 minutes and the resulting material cooled in an ice-bath while 2M NaCl solution was added in several portions. This product was further washed in several cycles with 1N NaOH and 1N HCl. DEAE-cellulose made from this procedure had 1.4% nitrogen content which corresponded to 1.0 meq/gram of exchanger. When used for protein separation and purification, Sober et al., (1956), and Sober and Peterson (1954), reported that good resolution was achieved at loads as high as 170 mg protein per gram of adsorbent. Other separations were reported by James and Stanworth (1964).

Peterson's method was improved by Guthrie and Bullock (1960) who crosslinked the cellulose prior to derivatization by soaking purified cotton linters for 1.5 hours in an aqueous solution of 10 parts by volume of 36% formaldehyde and 2 parts of concentrated (37%) hydrochloric acid. Reacting, crosslinking, and derivatizing the cellulose three times gave increasing N contents of 1.43, 2.95, and 4.56, respectively.

In spite of these efforts, a need has persisted for continuous stationary phase materials with high protein sorption capacity. The present invention addresses this need.

SUMMARY OF THE INVENTION

Briefly describing one preferred aspect of the present invention, there is provided a solid sorbent material comprising cellulose which has been modified by hydrolysis with a cellulase enzyme for a duration sufficient to increase the protein adsorption capacity of the solid sorbent material. Other aspects of the invention provide methods for preparing the solid sorbent material and methods for purifying a protein including passing a liquid medium containing the protein over the solid sorbent material.

It is an object of the present invention to provide modified sorbents with increased protein adsorption capacities and methods for preparing the sorbents.

It is another object of this invention to provide continuous stationary phases for liquid chromatography with improved protein sorption capacity.

It is a further object of the present invention to provide improved methods for purifying proteins.

A still further object is to provide a new class of high speed, non-particulate, cellulosic materials for chromatography.

A still further object of the invention is to provide chromatographic columns containing solid sorbent stationary phases having improved adsorption capacities.

These and other objects, advantages and features of the invention will be apparent from the following description.

DESCRIPTION OF THE PREFERRED EMBODIMENT

Figure 1:
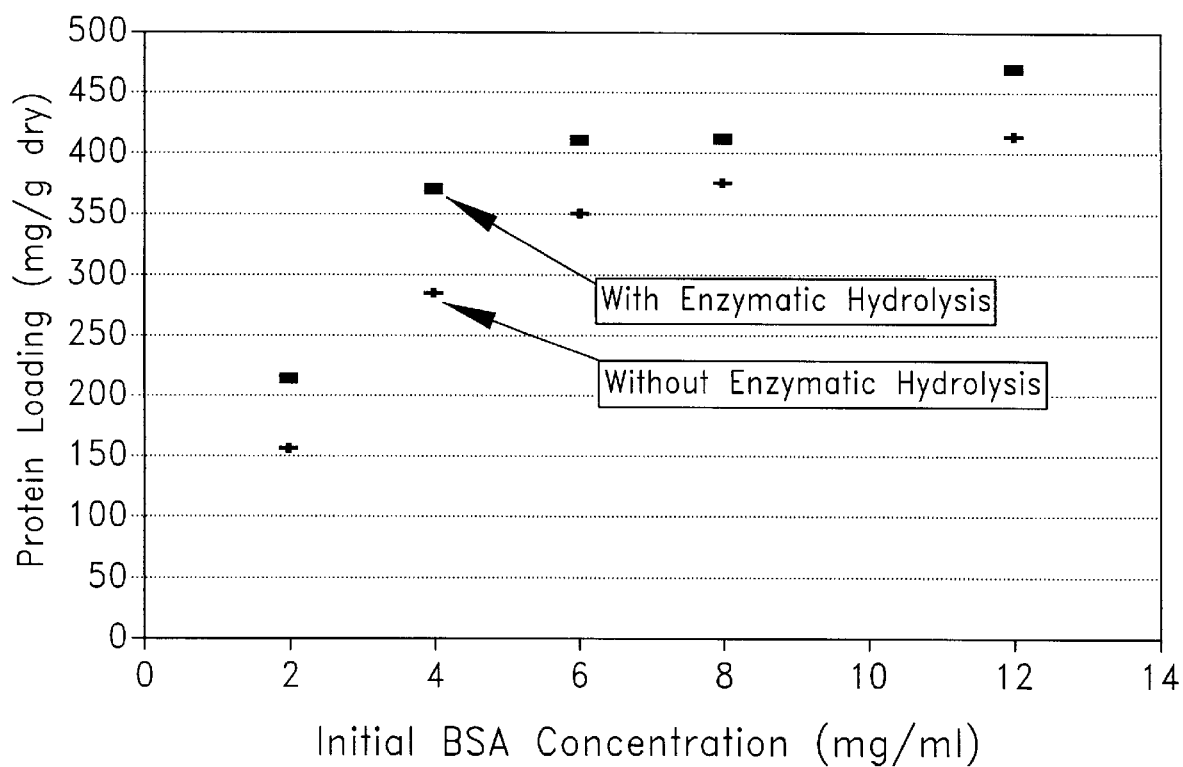
FIGS. 1 and 2 provide graphs illustrating the increased adsorption capacity of particulate cellulose stationary phases when treated in accordance with the invention.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications, and applications of the principles of the invention as illustrated herein being contemplated as would normally occur to one skilled in the art to which the invention relates.

The present invention provides cellulosic solid sorbent materials which have been modified by treatment with a cellulase enzyme to increase the protein adsorption capacity of the solid sorbent material. The current invention employs cellulase enzymes to facilitate penetration of other globular proteins into the internal regions of cellulose material.

A feature of the present invention is the discovery that cellulase-mediated hydrolysis of cellulose stationary phases, especially continuous stationary phases, can be used to significantly improve properties of the phases, for example leading to significantly improved adsorption capacities for globular proteins and other molecules. While prior uses of continuous stationary phases demonstrated excellent and rapid separations, accompanied by mechanical stability at eluent linear velocities in excess of 5000 cm/hr (Yang et al., 1992, 1993), protein sorption capacity was low and corresponded to less than 10 mg/g. The present invention addresses this problem by employing cellulase enzymes to modify the stationary phases so as to increase sorption capacity. While the present invention is not bound by any theory presented herein or otherwise, it is believed that the cellulase treatment increases the surface area accessible to macromolecules by increasing the porosity of the cellulose structure.

As to the cellulase enzyme, the particular enzyme employed is not critical to the broader aspects of the present invention. Such enzymes are produced by and can be obtained from suitable microorganisms such as fungi, e.g. *Aspergillus niger*, *Trichoderma viride*, or *Thielatia terrestris*, using conventional techniques, or can also be obtained from commercial sources. It is preferred that the cellulase enzyme employed have a molecular weight in the range of about 20,000 to about 100,000, more preferably about 50,000 or more. Such enzymes are believed to provide effectively-sized pores when acting upon cellulose, to improve adsorption capacities.

The modified sorbent materials of the present invention are useful inter alia as continuous stationary phases in liquid chromatography applications. The preferred sorbent material is cellulose based and may be particulate, fibrous or preferably, a continuous phase comprising a woven or non-woven fabric. Moreover, the sorbent material can be derivatized to introduce ionic or nonionic functional groups as well known and used in the art of chromatography to introduce cation exchange, anion exchange and/or affinity character to the sorbent. The derivatized sorbent material is preferably an amino-functionalized material such as a dialkylaminoalkyl cellulose, e.g. DEAE cellulose, although celluloses containing other functional groups such as sulfate, alkylsulfate, carboxymethyl, phosphate, quaternary salt or other beneficial groups can also be prepared in accordance with the invention. Alkyl groups in these functional groups typically contain 1 to about 5 carbon atoms. As one example, to prepare a preferred DEAE cellulose material, a cotton fabric can be immersed into a mixture of NaOH and DEAE for a period of several hours, for example about 6 to 10 hours. In such a process, the fabric to liquid ratio is preferably in the range of about 1:25 to about 1:50 W/V, and the concentration of DEAE is preferably up to about 1M.

According to the present invention, the solid sorbent material may include fibers of two different materials. For example, the sorbent may include a fabric comprising derivatized cellulose fibers, combined with another type of fiber designed to reinforce and improve the overall mechanical properties of the stationary phase. For example, derivatized cellulose and synthetic fibers such as polyester nylon or KEVLAR® aromatic polyamide fibers can be blended to achieve an advantageous stationary phase. The stationary phase may also include fibers of cellulose which have been separately derivatized with differing derivatizing agents, e.g. DEAE- and sulfate-derivatized cellulose fibers which have been blended together in a fabric.

As indicated above, the invention contemplates the hydrolysis of a cellulose based sorbent material with a cellulase enzyme for a duration sufficient to form the modified sorbent material with an increased protein adsorption capacity. According to one mode of carrying out the invention, the sorbent material is treated with the cellulase enzyme for up to about 6 hours at a pH of about 3 to about 8, more preferably a pH of about 4 to about 6. Temperatures during these treatments may vary so long as the temperature employed does not denature or otherwise inactivate the enzyme. Temperature of about 4° C. to about 80° C. are typical, and more preferably fall within the range of about 20° to about 60° C. A preferred hydrolysis protocol in work to date has included exposing the cellulosic material to the cellulase enzyme for about 1 hour at a pH of about 5 to about 6 and at a temperature of about 50° C.

The enzyme concentrations may also vary widely in treating the cellulosic material, for example ranging up to about 50 GCU/mL or more. More preferred cellulase enzyme concentrations are in the range of about 2 to about 10 GCU/mL. In this regard, one GCU is defined as one Genencor unit, which is equivalent to 1 FPU, a standardized level of enzyme activity based upon the rates at which strips of filter paper are hydrolyzed by cellulytic enzymes.

After the enzyme treatment, the enzyme is deactivated, for example by immersing the stationary phase in hot water to denature the enzyme. In this regard, when carrying out methods of the present invention, it is important that the cellulase-mediated hydrolysis be terminated prior to complete breakdown or fragmentation of the cellulose phase material, as this will provide materials having poor mechanical properties and/or which will lead to the collection of fines which deleteriously affect column performance. Preferred methods will be carried out so as to achieve stationary phases have breaking strengths of at least about 5 pound force (lbf), as described in the Examples below.

Preferred methods of the present invention also include a cellulose conditioning step which includes swelling the fabric or other cellulosic material in water or a solution of a swelling agent such as an organic or inorganic base, e.g. ammonia, ethylene diamine, or caustic. Sodium hydroxide (NaOH) solutions are preferred for these purposes. Pretreatment with swelling agents such as sodium hydroxide increases reactivity with respect to enzyme hydrolysis. This is believed to result in an increased internal porosity and surface area accessible to protein either directly (through swelling) or indirectly (by facilitating enzyme attack).

Optionally, the cellulose conditioning step may also include a prederivatization step. Cellulose prederivatization may be accomplished for example, by immersing a cellulose based material in a mixture of NaOH and a derivatizing agent such as 2-(diethylamino)ethyl chloride (DEAE-Cl). After conditioning and/or prederivatization, the fabric can be washed, for example with with deionized water, prior to further treatment with the cellulase enzyme.

Once prepared, the stationary phases of the invention can be packed into metal, plastic, glass or other columns suitable for use in liquid or other chromatographic techniques. For example, to pack a modified, rolled continuous phase of the invention, an aperture can be punched or drilled in the end of the phase, and a cord made from a material having a high tensile strength, e.g. KEVLAR® aromatic polyamide fiber, can be threaded through the aperture. The cord can then be threaded through the column and used to pull the phase into the column, for example employing a winch or similar mechanized device as described in copending U.S. patent application of Michael Ladisch et al. entitled DEVICE FOR PACKING CHROMATOGRAPHY PHASES, filed Jun. 15, 1994, which is hereby incorporated herein by reference in its entirety. Preferred columns so produced will have packing densities of at least about 0.5 g/cc, usually in the range of 0.5 to 0.6 g/cc. As well, preferred columns will have void fractions as low as about 0.4 and even ranging to about 0.3 or lower.

Once packed in the column, the stationary phases of the invention can be employed in liquid chromatography to separate or purify a wide variety of proteins or other molecules of interest in the biotechnological and other arts. Thus, the present invention also includes methods for separating proteins or other molecules, wherein a liquid mobile phase containing the protein or other molecule is passed over a modified cellulosic stationary phase material of the invention and a purified fraction containing the protein or other molecule is recovered. Columns of the invention, when so used, have highly advantageous flow properties, for example providing stability at linear flow velocities readily exceeding 50 cm/min and even ranging up to about 100 cm/min or more. Rapid, efficient separations are thereby provided by columns of the present invention.

In order to promote a further understanding of the invention and appreciation of its features and advantages, the following specific Examples are provided. It will be understood that these Examples are illustrative and not limiting of the invention.

EXAMPLE 1

One-Step Procedure: Derivatization

Cotton fabric was soaked in 18% NaOH in an ice bath overnight and then reacted with various concentrations of DEAE-Cl (added to the NaOH) at 22° C. for 1 hour. The fabric to liquid ratio was 1:50. The concentration of DEAE varied from none to 1M. The fabric was washed and then tested with respect to protein (BSA) loading using a BSA concentration of 2 mg/mL at pH 8.4 (10 mM Tris). Adsorption was carried out using fabric pieces weighing ca. 120 mg in contact with 5 mL of BSA solution at room temperature for 6 hours. Table 1 shows that the optimum DEAE-Cl concentration in these runs was 0.5M, achieving a capacity of 26.7 mg/g.

TABLE 1

Effect of DEAE-Cl Concentration
on BSA Adsorbtion by Derivatized Fabric
(Stationary Phase Equilibrated with 2 mg/mL BSA
for 6 Hours at 22° C.)

| DEAE (M) | mg/dry g |
|---|---|
| 0.25 | 12.4 |
| 0.50 | 26.7 |

TABLE 1-continued

Effect of DEAE-Cl Concentration
on BSA Adsorbtion by Derivatized Fabric
(Stationary Phase Equilibrated with 2 mg/mL BSA
for 6 Hours at 22° C.)

| DEAE (M) | mg/dry g |
|---|---|
| 1.0 | 9.1 |
| 2.0 | 6.0 |

EXAMPLE 2

Two-Step Procedure:

Enzymatic Treatment followed by Derivatization With DEAE

Cellulose fabric was washed and then incubated with cellulase enzyme (CYTOLASE Cl cellulase enzyme from Genencor) for 1 hour at 50° C. The cotton fabric was derivatized after enzyme treatment using 0.5 M DEAE-Cl in 18% NaOH at 22° C. for 6 hours. Three samples with various enzyme concentrations and pH were analyzed, and the results are set forth in Table 2.

TABLE 2

Effect of Enzyme Concentration
On Derivatization Procedure at pH 4.9 and 5.9

| Enzyme (GCU/mL) | pH | Protein Loading (mg/dry g) | Breaking Strength (lbf.) |
|---|---|---|---|
| 0 | 4.9 | 6.0 | 57 |
| 1.8 | 4.9 | 11.5 | 47 |
| 3.6 | 4.9 | 20.2 | 50 |
| 0 | 5.9 | 6.5 | 52 |
| 9.0 | 5.9 | 20.6 | 46 |

The loading increased with increasing enzyme concentration. The breaking strength was, at most, moderately affected over the range of enzyme concentrations and pH shown in Table 2. In this regard, the breaking strength was taken as a first measure of the robustness of the material when rolled and placed into an LC column.

EXAMPLE 3

Three-Step Procedure:

Conditioning, Enzyme Hydrolysis, and Derivatization With DEAE

The cellulose material was conditioned by swelling it in water or 18% NaOH, or by prederivatizing and washing. The conditioned fabric was treated with 18 GCU/ml enzyme (CYTOLASE Cl cellulase enzyme, Genencor) at either pH 4.9 or pH 5.9 and 50° C. for 1 hour. The hydrolyzed fabric was throughly washed and then immersed into boiling water for about 5 minutes to denature the enzyme. The fabric was then immersed in a mixture of 0.5M DEAE-Cl and 18% NaOH for 6 hours at room temperature. The results are presented in Table 3.

TABLE 3

Three-Step Procedure:
Effect of Sodium Hydroxide During Cellulose Conditioning

| Conditioning | Protein Loading (mg/g) | Breaking Strength (1 bf.) |
|---|---|---|
| Water Only | 21 | 46 |
| 18% NaOH, 6 hours | 42 | 6 |

As Table 3 demonstrates, the protein adsorption capacity of the sorbent was dramatically increased to 42 mg/g with the NaOH treatment, while the breaking strength was somewhat lowered but nevertheless the material remained sufficiently stable for advantageous use as a stationary phase.

Experiments also demonstrated that prederivatization with DEAE facilitates high protein loading. This is illustrated by the data in Table 4, which presents the effect of the concentration of DEAE-Cl in 18% NaOH during prederivatization for 6 hours.

TABLE 4

Effect of pH and Enzyme Treatment on Loading of BSA

| Run | Enzyme Conc. (GCU/mL) | pH of Enzyme Treatment | % NAOH | DEAE-Cl (M) | Protein Adsorption Capacity mg/g | Break Strength 1 bf. |
|---|---|---|---|---|---|---|
| a | 0.0 | 5.9 | 18 | 0.0 | 13 | 55 |
| b | 0.0 | 4.9 | 18 | 0.0 | 24 | NA |
| c | 0.0 | 4.9 | 18 | 0.5 | 77 | NA |
| d | 9.0 | 5.9 | 18 | 0.0 | 42 | 6 |
| e | 18.0 | 4.9 | 18 | 0.0 | 84 | NA |
| f | 18.0 | 4.9 | 18 | 0.5 | 120 | 5 |

NA = Not Assayed

As shown, when the concentration of enzyme is 18.0 GCU/ml, increasing the concentration of 2-(diethylamino) ethyl chloride from 0 to 0.5M results in an increase of protein adsorption capacity from 84 to 120 mg/g. When no enzyme is used, increasing the concentration of 2-(diethylamino)ethyl chloride from 0 to 0.5M still increases protein adsorption capacity from 24 to 77 mg/g.

EXAMPLE 4

Protein Adsorption Capacity and Break Strength

Cellulase-treated fabric and non-treated samples were swelled in 18% NaOH. Some samples were derivatized with DEAE generally as described in the examples above. The samples were compared for protein adsorption capacity and break strength.

When derivatization with DEAE was preceded by swelling the fabric in 18% NaOH, loadings were on the order of 13 to 24 mg/g for an initial protein concentration of 2 mg/mL (Table 4, runs a and b). The loading increased almost 100% to 42 mg/g (run d) with NaOH pretreatment and derivatization with a moderate level of enzyme. Run e shows that doubling the enzyme concentration at a pH close to that required for maximum enzyme activity yields a material with a protein loading of 84 mg/g. This gives a loading which is similar to that for DEAE cellulose which was pretreated (swollen) in 18% NaOH, pretreated/derivatized with DEAE, washed, and then derivatized a second time in a solution of 18% NaOH and 0.5M DEAE-Cl (see run b in Table 4). Run f again shows the unexpected efficacy of the cellulose enzyme, where treatment with the enzyme, after derivatization, dramatically increases loading to 120 mg/g, with loading again measured for an initial BSA concentration of 2 mg/mL.

Loading capacity of this material (as prepared in run f) was further characterized by measuring protein loading at initial BSA concentrations from 2 to 16 mg/mL at pH 8.4, 10 mM Tris, 22° C. (see Table 5 below). In these experiments a loading of 225 mg/g was achieved. The packing density of the continuous stationary phase is on the order of 0.6 g stationary phase (dry basis) per mL of column volume. On this basis 225 mg/g translates to 132 mg/mL. It has thus been demonstrated that the invention provides dramatic, high protein loadings which translate to improvements in chromatographic efficiency and other important parameters, particularly in preparative and commercial scale operations.

EXAMPLE 5

Figure 2:
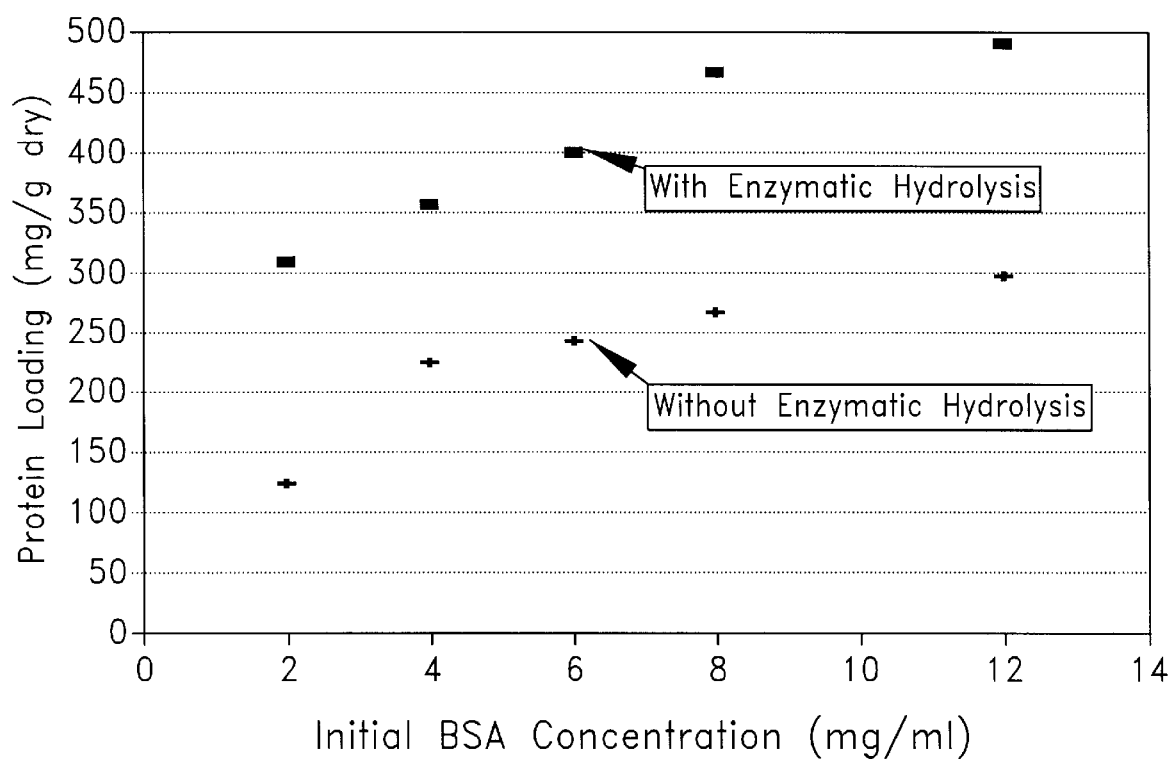

Comparison of BSA Loading of Fibrous, Microgranular and Cellulase Treated Fabric The BSA loading capacities of Microgranular fibrous and cellulase treated fabric cellulose materials were measured and compared using a static loading procedure in which the cellulose, or a strip of fabric, was incubated in test tubes containing initial BSA concentrations of 1.96 to 15.64 mg/ml in 10 mM Tris buffer at pH 8.4. The results in Table 5 clearly show that all three DEAE cellulose materials have excellent loading. Because particulate materials have limited flow ranges, a fabric based, rolled stationary phase provides tremendous advantages in preparative and commercial scale separations.

and, alongside the corresponding unmodified phases as obtained from the manufacturer, were tested for protein adsorption capacity in accordance with the procedures described in Example 1 above, except that a range of protein concentrations was used. The results of these tests for the modified DE 3764 and DE 0909 phases are set forth in FIGS. 1 and 2, respectively. As the Figures demonstrate, the methods of the invention provided modified particulate phases having substantially improved protein adsorption capacities as compared to the unmodified materials.

EXAMPLE 7

Derivatization of 60/40 Cotton/Polyester Fabric

A. Pretreatment

Preparation of fabric: 60/40 (g/g) cotton/polyester fabric (from Cotton Corporation, Inc.) is stored in a 67°–73° F. and 60–70% relative humidity conditional room. The fabric is placed in the conditioning room for at least 3 days before it is cut and weighed for pretreatment.

Preparation of 18% NaOH solution: A solution of 18% NaOH is made by dissolving 175.6 gram solid sodium hydroxide into 800 ml D.I. water. In order to minimize evaporation of water, the beaker is immersed into ice water to keep temperature at 0° C. during the solution preparation.

Preparation of pretreatment solution: The 18% NaOH is first measured with a volumetric cylinder and transferred into an Ahiba container (Ahiba containers are designed for Ahiba dyeing machine used to carry out the DEAE derivatization procedures). Next, 0.5M 2-(diethylamino) ethyl chloride (DEAE-Cl, MW 172) (from SIGMA) is added into the NaOH solution. The amount of DEAE-Cl is calculated on the volume of 18% NaOH solution instead of on the total

TABLE 5

Summary of Static Loading Experiments for BSA

|  | DE-52 (Microgranular) | | DE-23 (Fibrous) | | This Work (Fabric) | |
| --- | --- | --- | --- | --- | --- | --- |
| Initial BSA (mg/ml) | Final BSA* (mg/ml) | Loading** (mg/g) | Final BSA* (mg/ml) | Loading** (mg/g) | Final BSA* (mg/ml) | Loading** (mg/g) |
| 1.96 | 0.24 | 173 | 0.34 | 153 | 0.29 | 122 |
| 3.91 | 1.10 | 282 | 1.57 | 222 | 1.62 | 168 |
| 5.87 | 2.40 | 349 | 3.32 | 241 | 3.25 | 192 |
| 7.82 | 4.10 | 375 | 5.02 | 265 | 5.16 | 195 |
| 11.73 | 7.61 | 413 | 8.64 | 295 | 8.94 | 205 |
| 15.64 | 10.37 | 531 | 11.78 | 366 | 12.58 | 225 |

Conditions: pH 8.4, 10 mM Tris buffer at room temperature (22° C.) for 6 hours. Cellulose concentrations of 9.92 mg/mL for DE-52; 10.6 mg/mL for DE-23; 13 to 14 mg/mL for Fabric
*Liquid phase at equilibrium
**Solid phase at equilibrium

EXAMPLE 6

Modification of Particulate Phases

Experiments were conducted to demonstrate that particulate stationary phases can also be advantageously modified in accordance with the invention. The starting materials were particulate DEAE cellulose stationary phases commercially available from Whatman of Hillsboro, Oreg., 97123, under the designations DE 3764 and DE 0909. These materials were subjected to cellulase-mediated hydrolysis using a hydrolysis procedure as set forth in Example 2 above, except that further DEAE derivatization, after enzyme treatment, was omitted. The resulting modified particulate phases appeared to maintain structural integrity, volume after the DEAE-Cl is added. The pretreatment solution is prepared for each fabric on an individual basis at a NaOH solution to fabric ratio of 50 to 1 (ml:g).

Pretreatment: The fabric is first wetted with D.I. water and then the water is squeezed out by hand. The pretreatment procedure consists of immersing fabric into the pretreatment solution in the Ahiba container at room temperature, installing the Ahiba container into the dyeing machine, and rotating the container, for a specified length of time. For temperature control purposes, the liquid in the Ahiba dyeing machine is heated to 40° C. before the container is immersed. After 6 hours of pretreatment, the machine is stopped, and the fabric is removed, and rinsed repeatedly in D.I. water.

B. Enzymatic Hydrolysis

Preparation of citrate buffer: Citrate buffer (1M) is made by mixing 210 g citric acid monohydrate ($C_6H_8O_7 \cdot H_2O$) into 750 ml D.I. water. About 60 g NaOH is then added to this mixture until a pH 4.3 is obtained. The mixture is then adjusted to 1 liter. After measuring the pH again, more NaOH is added until a pH of 4.5 is obtained. When diluted to 0.05M, the buffer's pH is 4.8.

Preparation of enzyme solution: An enzyme solution containing 9 GCU cellulase is made by mixing 9 parts of 50 mM citrate buffer (pH 4.8) with 1 part of CYTOLASE™ 123 cellulase enzyme (from Genecor, Inc.) immediately before use. The total volume of enzymatic solution to weight of fabric is 30 to 1 (ml:g).

Hydrolysis: Hydrolysis consists of squeezing water out from the wet pretreated fabric by hand, immersing the fabric into enzymatic solution in the Ahiba container, installing the Ahiba container into the dyeing machine, and rotating the container for a specified time. The solution in the container is heated to 50° C. prior to hydrolysis. After 1 hour hydrolysis at 50° C., the machine is stopped, and the fabric is removed and rinsed in D.I. water for a few minutes. Then the fabric is placed into boiling water for 5 minutes to deactivate the enzyme, followed by repeated rinsing in D.I. water at room temperature.

C. Derivatization of Hydrolyzed Fabric

Preparation of Derivatization solution: 18% NaOH solution is measured using a volumetric cylinder and transferred into an Ahiba container. 0.5M DEAE-Cl (from SIGMA) is then added into the NaOH solution. The amount of DEAE-Cl is calculated on the volume of 18% NaOH solution, as before. This derivatization solution is prepared each time a new batch of fabric is to be treated. The ratio of 18% NaOH solution to weight of fabric is 50 to 1 (ml:g).

Derivatization: Water in the fabric is squeezed out. The derivatization procedure consists of immersing hydrolyzed fabric into the derivatization solution at room temperature, installing the Ahiba container into the Ahiba dyeing machine, and rotating the container for a specified time. The solution in Ahiba dyeing machine is heated to 40° C. before the container is immersed. After 6 hours derivatization, the machine is stopped, and the fabric removed and rinsed repeatedly with D.I. water.

D. Results

Figure 3:
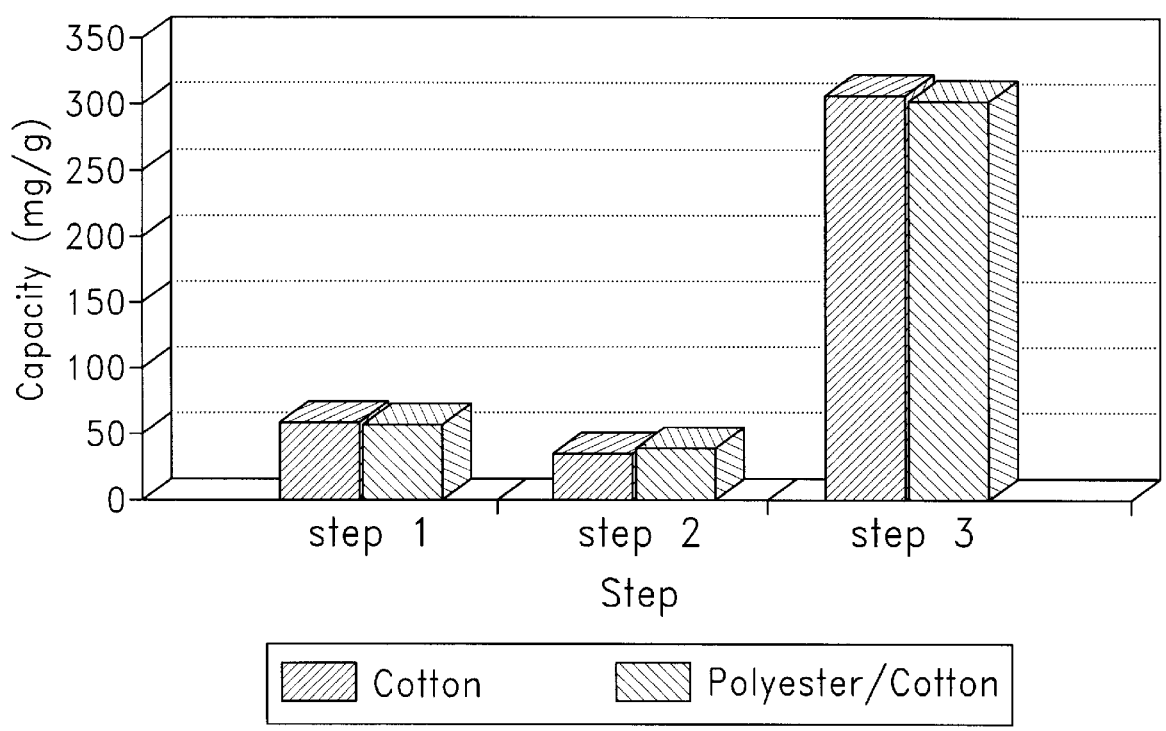
FIGS. 3 and 4 provide graphs comparing the adsorption capacities and break strengths, respectively, of cotton and cotton/polyester blend stationary phases when treated in accordance with the invention.
Figure 4:
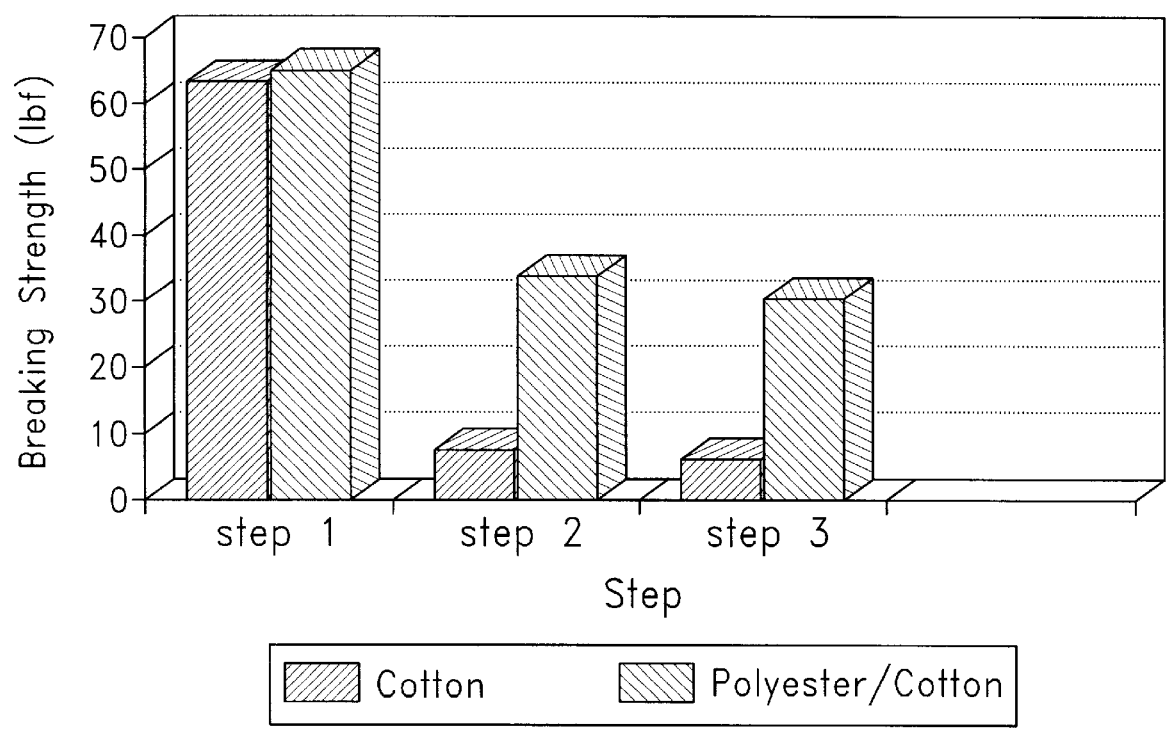

The benefit of this approach is illustrated in FIGS. 3 and 4 which compare capacity and breaking strengths of the two types of fabric: cotton and 40% polyester/60% cotton. A break strength of 30 lbs. gives a stable column in which the stationary phase, when appropriately rolled and packed, will withstand linear eluent velocities of at least 50 cm/min. The cotton/polyester material has a protein (BSA) loading capacity which is similar to cotton. This, together with its enhanced strength, make the cotton/polyester material highly advantageous as a stationary phase for liquid chromatography.

REFERENCES

The following references are hereby incorporated herein by reference as if each had been individually incorporated by reference and fully set forth.

Guthrie, J. D., and Bullock, A. L., Ion Exchange Celluloses for Chromatographic Separation, *Ind. Eng. Chem.*, 52, 935–937 (1960).

Hartman, M., U.S. Pat. No. 1,777,970 (1930).

Hoffpauir, C. L., and Guthrie, J. D., Ion-Exchange Characteristics of Chemically Modified Cotton Fabrics, *Textile Res. J.*, 20, 617–620 (1950).

James, K., and Stanworth, D. R., Studies on the Chromatography of Human Serum Protein on Diethylamino-ethyl (DEAE) - Cellulose I. The Effect of the Chemical and Physical Nature of the Exchanger, *J. Chromatogr.*, 15, 324–335 (1964).

Knight, C. S., Some Fundamentals of Ion-Exchange-Cellulose Design and Usage in Biochemistry. Advances in Chromatography V. 4, Giddings, J. C., and Keller, R. A. (eds.), Marcel Dekker, Inc., New York, N.Y., 1967, 61–110.

Peterson, E. Q., and Sober, H. A., Chromatography of Proteins. I. Cellulose Ion-Exchange Adsorbents, *J. Am. Chem. Soc.*, 78, 751–755 (1956).

Roberts, E. J., Bose, J. L., and Rowland, S. P., Evidence for Two Types of Accessible Surfaces in Fibrous Cotton, *Textile Res. J.*, 42, 217–221 (1972).

Rowland, S. P., Roberts, E. J., and Wade, C. P., Selective Accessibilities of Hydroxyl Groups in the Microstructure of Cotton Cellulose, *Textile Res. J.*, 39, 530–542 (1969).

Roy, D., and Konigsberg, W., Chromatography of Proteins and Peptides on Diethylaminoethyl Cellulose, in Methods in Enzymology Vol. 25, Hirs, C.H.W. (ed.), Academic Press, New York, N.Y., 1972, pp. 221–231.

Sober, H. A., and Peterson, E. A., Chromatography of Proteins on Cellulose Ion-Exchangers, *J. Am. Chem. Soc.*, 76, 1711–1712 (1954).

Sober, H. A., Gutter, F. J., Wyckoff, M. M., and Peterson, E. A., Chromatography of Proteins. II. Fractionation of Serum Protein on Anion-exchange Cellulose, J. Am. Chem. Soc., 78, 756–763 (1956).

Soignet, D. M., Berni, R. J., and Benerito, R. R., Comparison of Properties of Anion-Exchange Cottons in Fabric Form, *Textile Res. J.*, 30, 978–989 (1966).

Tsuei, A.C.R., and Yang, V. C., Ion-Exchange Hollow Fibers, *Polymer Preprints*, 31, 238–239 (1990).

Yang, Y., Velayudhan, A., Ladisch, C. M., and Ladisch, M. R., Protein Chromatography Using a Continuous Stationary Phase, *J. Chromatogr.*, 598, 169–180 (1992).

Yang, Y. Velayudhan, A., Ladisch, C. M., and Ladisch, M. R., Liquid Chromatography Using Cellulosic Continuous Stationary Phases, *Adv. Bioeng. Biotechnol*, 49, 147–160 (1993).

While the invention has been described in detail in the foregoing description, the same is to be considered as illustrative and not restrictive in character, it being understood that only the preferred embodiments have been shown and described, and that all changes and modifications that come within the spirit of the invention are desired to be protected.

What is claimed is:

1. A composition for use as a chromatographic stationary phase, comprising:
a fabric comprising cellulose which has been modified by hydrolysis with a cellulase enzyme for a duration sufficient to increase the protein adsorption capacity of the fabric relative to the protein adsorption capacity of the fabric prior to said hydrolysis, said fabric having also been derivatized to introduce cation exchange, anion exchange and/or affinity functional groups.

2. The composition of claim 1 wherein the fabric comprises functional groups selected from the group consisting of amino, sulfate, alkylsulfate, carboxymethyl, phosphate and quaternary salt functional groups.

3. The composition of claim 2 wherein the fabric comprises amino or sulfate functional groups.

4. The composition of claim 2 wherein the fabric comprises dialkylaminoalkyl functional groups.

5. The composition of claim 4 wherein the fabric comprises diethylaminoethyl functional groups.

6. The composition of claim 1 wherein the fabric comprises a blended fabric of cellulose and synthetic fibers.

7. A method for purifying a protein, comprising:

passing a liquid medium containing the protein over a solid sorbent material comprising cellulose which has been modified by hydrolysis with a cellulase enzyme for a duration sufficient to increase the protein adsorption capacity of the solid sorbent material, and recovering therefrom a fraction containing the purified protein.

8. A method for purifying a protein, comprising:

passing a liquid medium containing the protein over a cellulosic fabric having diethylaminoethyl functional groups and having an adsorption capacity of at least about 50 mg protein/g sorbent material as measured with bovine serum albumin, and recovering therefrom a fraction containing the purified protein.

9. A chromatographic column containing a stationary phase according to claim 1.

10. The method of claim 7 wherein the sorbent material comprises ionic or nonionic functional groups.

11. The method of claim 10 wherein the functional groups are diethylaminoethyl groups.

12. The method of claim 7 wherein the sorbent material is a fabric.

13. The method of claim 12 wherein the fabric comprises a blended fabric of cellulose and synthetic fibers.

14. The chromatographic column of claim 9 wherein: said stationary phase includes a rolled sheet of cellulosic fabric.

15. The chromatographic column of claim 14 wherein said cellulosic fabric has been derivatized to incorporate functional groups selected from the group consisting of amino, sulfate, alkylsulfate, carboxymethyl, phosphate and quaternary salt functional groups.

16. The chromatographic column of claim 15 wherein said cellulosic fabric has been derivatized to incorporate diethylaminoethyl functional groups.

17. A chromatographic column, comprising:

a column;

a stationary phase packed in said column, said stationary phase including a rolled sheet of cellulosic fabric; and wherein said cellulosic fabric is the product of a process which comprises (i) hydrolyzing a first cellulosic fabric with a cellulase enzyme, and (ii) terminating said hydrolyzing step after a duration sufficient to form a modified cellulosic fabric having an increased adsorption capacity for bovine serum albumin relative to the first cellulosic fabric prior to the hydrolysis with the cellulase enzyme.

18. The column of claim 17, wherein said cellulosic fabric has been modified to introduce cation exchange, anion exchange and/or affinity chromatography functional groups.

19. The column of claim 18, wherein said cellulosic fabric has been modified to introduce diethylaminoethyl functional groups.

* * * * *

UNITED STATES PATENT AND TRADEMARK OFFICE
CERTIFICATE OF CORRECTION

PATENT NO. : 5,808,010
DATED : September 15, 1998
INVENTOR(S) : Michael Ladisch et al.

It is certified that error appears in the above-identified patent and that said Letters Patent is hereby corrected as shown below:

On the cover page, Section 54, please delete "PHASE" and insert in lieu thereof --PHASES--.

In col. 2, line 7, please delete the comma after "almost".

In col. 8, line 7, please delete "(1 bf.)" and insert in lieu thereof --(1bf.)--.

In col. 8, line 30, please delete "1 bf." and insert in lieu thereof --1bf.--.

Signed and Sealed this

Seventh Day of September, 1999

Attest:

Q. TODD DICKINSON

Attesting Officer

Acting Commissioner of Patents and Trademarks